US 8,246,803 B2

Aug. 21, 2012

(12) United States Patent
Yamazaki et al.

(54) CAPILLARY ELECTROPHORESIS APPARATUS AND ELECTROPHORESIS METHOD

(75) Inventors: Motohiro Yamazaki, Mito (JP); Ryoji Inaba, Hitachinaka (JP); Satoshi Takahashi, Hitachinaka (JP); Shigeru Matsui, Hitachinaka (JP)

(73) Assignee: Hitachi High Technologies Corporation, Tokyo (JP)

( * ) Notice: Subject to any disclaimer, the term of this patent is extended or adjusted under 35 U.S.C. 154(b) by 892 days.

(21) Appl. No.: 11/654,683

(22) Filed: Jan. 18, 2007

(65) Prior Publication Data
US 2007/0170063 A1 Jul. 26, 2007

(30) Foreign Application Priority Data
Jan. 25, 2006 (JP) .................. 2006-016552

(51) Int. Cl.
*G01N 27/453* (2006.01)

(52) U.S. Cl. ......... 204/452; 356/344; 356/432; 204/603

(58) Field of Classification Search ............... 204/601, 204/452, 603; 356/344, 432–444
See application file for complete search history.

(56) References Cited

U.S. PATENT DOCUMENTS

| | | | |
|---|---|---|---|
| 5,630,924 A | 5/1997 | Fuchs et al. | |
| 5,948,231 A | 9/1999 | Fuchs et al. | |
| 6,017,765 A | 1/2000 | Yamada et al. | |
| 6,821,402 B1 | 11/2004 | Sharaf et al. | |
| 6,863,791 B1 | 3/2005 | Liu et al. | |
| 6,936,152 B2 * | 8/2005 | Kojima et al. | 204/601 |
| 2002/0176069 A1 * | 11/2002 | Hansen et al. | 356/73 |
| 2003/0054569 A1 | 3/2003 | Cheng et al. | |
| 2003/0178312 A1 | 9/2003 | Amirkhanian et al. | |
| 2004/0072335 A1 * | 4/2004 | Boege et al. | 435/287.2 |
| 2004/0160603 A1 * | 8/2004 | Reel | 356/328 |
| 2007/0163882 A1 * | 7/2007 | Yamazaki et al. | 204/451 |
| 2007/0259338 A1 | 11/2007 | Cheng et al. | |

FOREIGN PATENT DOCUMENTS

| | | |
|---|---|---|
| JP | 3-264859 | 11/1991 |
| JP | 5-52810 A | 3/1993 |
| JP | 10-239278 | 9/1998 |

(Continued)

OTHER PUBLICATIONS

Lewis et al. "Color-blind fluorescence detection for four-color DNA sequencing" PNAS Apr. 12, 2005, vol. 102, No. 15 p. 5346-5351.*

(Continued)

*Primary Examiner* — Kaj K Olsen
*Assistant Examiner* — Susan D Leong
(74) *Attorney, Agent, or Firm* — McDermott Will & Emery LLP

(57) ABSTRACT

An object of the present invention is to provide a capillary electrophoresis apparatus in which simultaneity can be ensured between sensitivity and data acquisition to decrease a pull-up signal while spectral data acquisition is eliminated in each capillary exchange. The invention relates to a capillary electrophoresis apparatus characterized in that a multi-bandpass filter is provided in an optical detection system. In one aspect of the invention, a signal detection area of a two-dimensional detector is divided into plural regions corresponding to wavelength transmission regions of the multi-bandpass filter. An integrated value of the fluorescence spectrum signal is determined in the region including a fluorescence spectrum peak of an analysis sample in the plural regions. The analysis is performed with the integrated value.

27 Claims, 10 Drawing Sheets

FOREIGN PATENT DOCUMENTS

| | | |
|---|---|---|
| JP | 2833119 B2 | 10/1998 |
| JP | 10-512371 | 11/1998 |
| JP | 11-108889 | 4/1999 |
| JP | 2005-502871 | 1/2005 |

OTHER PUBLICATIONS

Japanese Office Action issued in Japanese Patent Application No. JP 2006-016552 dated Oct. 26, 2010.

* cited by examiner

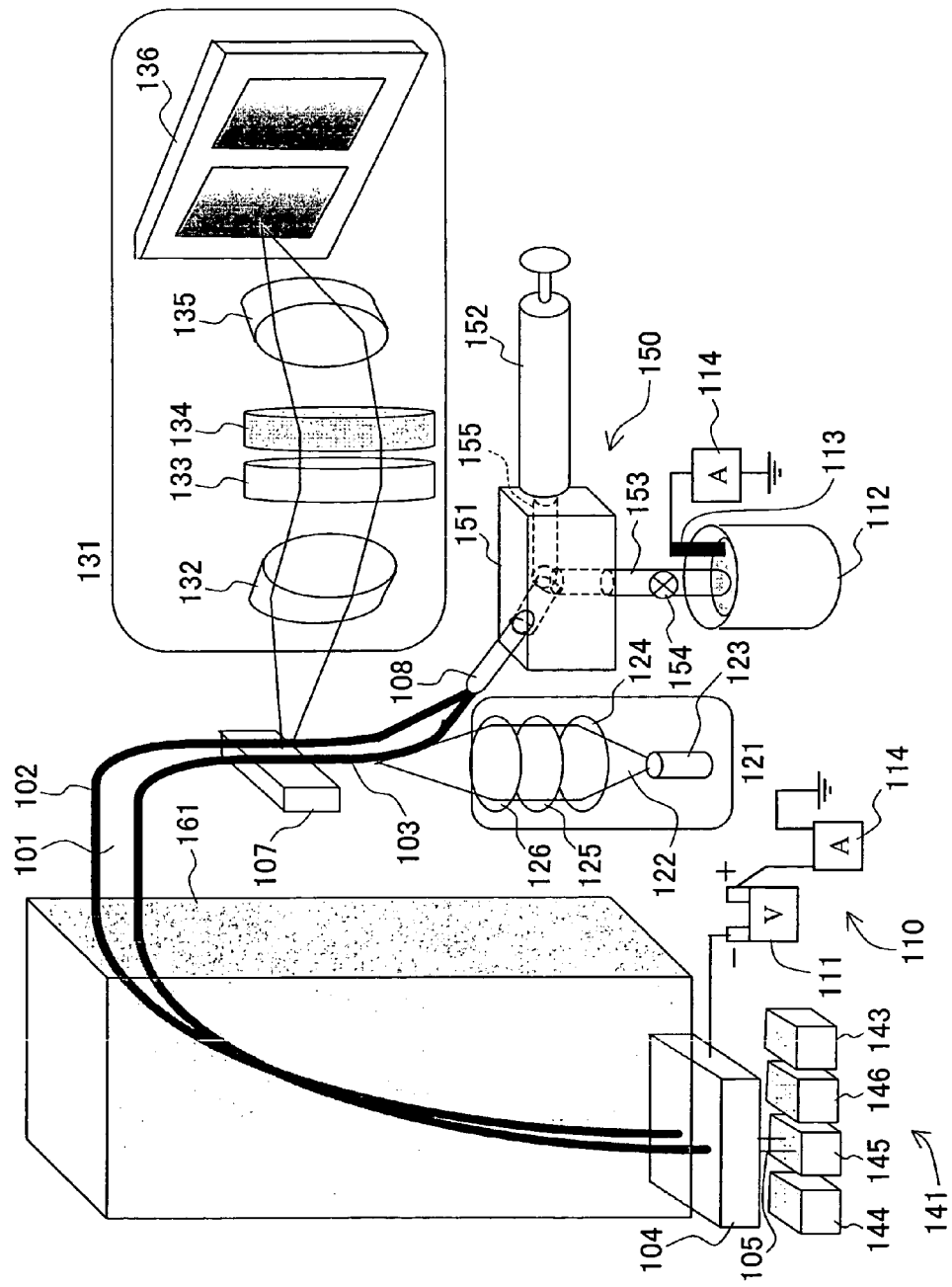
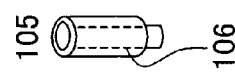

PARALLEL MOVEMENT

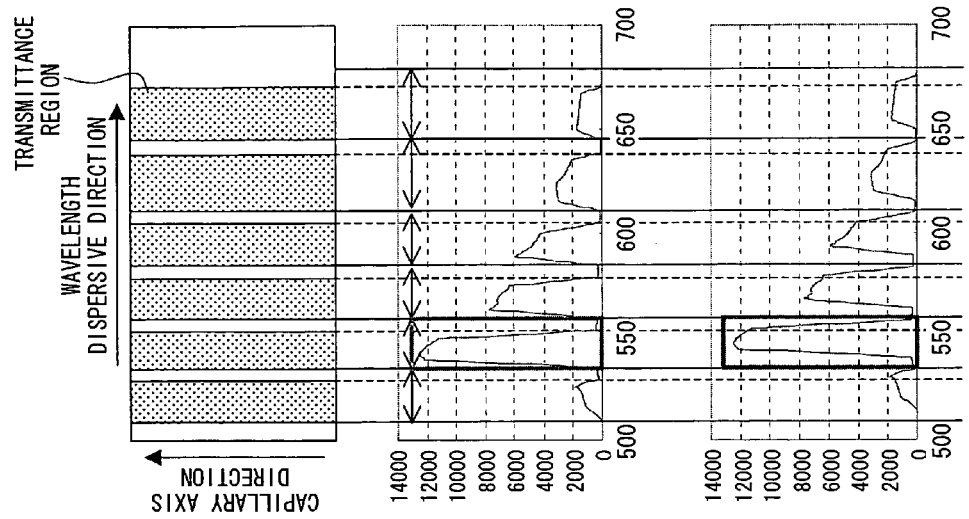
FIG. 7D
FIG. 7E
FIG. 7F
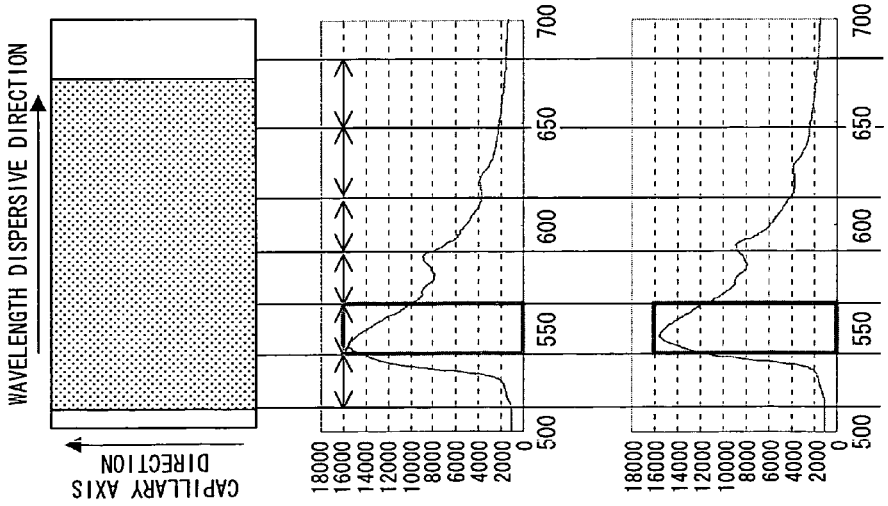
FIG. 7A
FIG. 7B
FIG. 7C

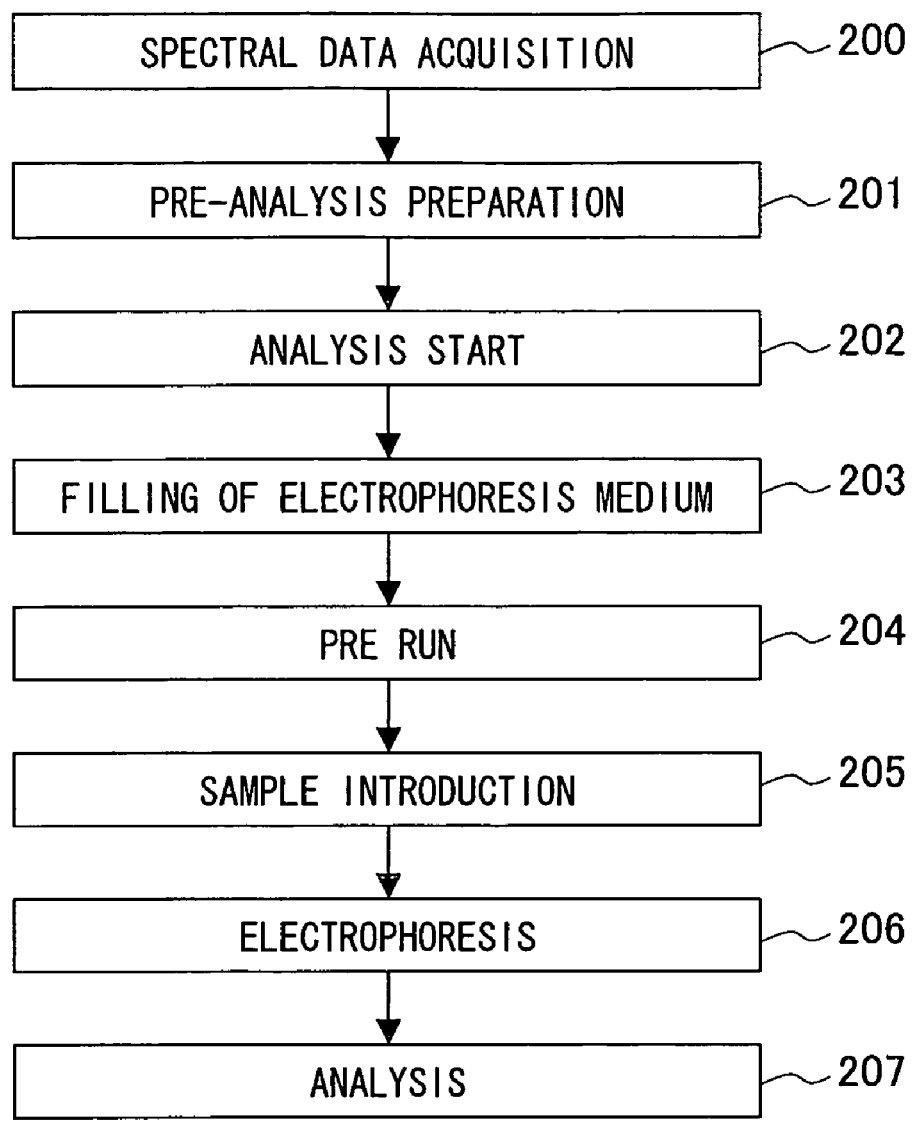

CAPILLARY ELECTROPHORESIS APPARATUS AND ELECTROPHORESIS METHOD

BACKGROUND OF THE INVENTION

1. Field of the Invention

The present invention relates to an electrophoresis apparatus in which nucleic acid, protein, or the like is separated and analyzed by electrophoresis, particularly to a capillary electrophoresis apparatus.

2. Description of the Related Art

Usually a laser light source is used as an excitation light source in the capillary electrophoresis apparatus. However, recently use of a light emitting diode (LED) for the excitation light source is propose to reduce cost of the capillary electrophoresis apparatus. USP 2003/0178312-A1 discloses an electrophoresis apparatus in which LED is used.

Japanese Patent Application Laid-Open No. 5-52810 and Japanese Patent No. 2833119 disclose an electrophoresis apparatus in which the laser beam is not emitted in a direction perpendicular to a capillary axis, but excitation light is emitted in a capillary axis direction. The excitation light propagates through the capillary to excite a detection target substance migrating in the capillary without imposing any restriction on a position of the detection target substance. A wide excited region, i.e., a wide detected region is acquired, which allows sensitivity to be enhanced in the electrophoresis apparatus. The detection light from a linear light emission portion is dispersed with a diffraction grating and detected with a two-dimensional detector.

U.S. Pat. Nos. 6,821,402 and 6,863,791 disclose a conventional method of acquiring spectral data.

Earnest study of inventor reveals the following problems. In the electrophoresis apparatus disclosed in Japanese Patent Application Laid-Open No. 5-52810 and Japanese Patent No. 2833119, because the capillary in itself is used as both an excitation unit and a detection unit, there is generated the problem that a detection position is shifted by capillary exchange. Therefore, it is necessary to acquire spectral data in each capillary exchange. When the spectral data is incorrect, a pull-up signal is generated in an analysis process due to the wavelength shift. With increasing wavelength shift, the pull-up signal is increased to reduce reliability of analysis result.

In the spectral data acquiring method disclosed in U.S. Pat. Nos. 6,821,402 and 6,863,791, the actual electrophoresis is required for a known sample, which takes a large amount of time for an operator.

That is, in the method in which the diffraction grating is used, the spectral data acquisition is required in each capillary exchange while the simultaneity can be ensured between the sensitivity and the data acquisition. On the other hand, in the method in which the plural filters are used, the simultaneity cannot be ensured between the sensitivity and the data acquisition while the spectral data acquisition is eliminated in each capillary exchange.

In view of the foregoing, an object of the invention is to provide a capillary electrophoresis apparatus in which the simultaneity can be ensured between the sensitivity and the data acquisition to decrease the pull-up signal while the spectral data acquisition is eliminated in each capillary exchange.

SUMMARY OF THE INVENTION

The invention relates to an electrophoresis apparatus characterized in that a multi-bandpass filter is provided in an optical detection system.

According to the invention, a signal detection area of a two-dimensional detector is divided into plural regions corresponding to wavelength transmission regions of the multi-bandpass filter. An integrated value of the fluorescence spectrum signal is determined in the region including a fluorescence spectrum peak of an analysis sample in the plural regions. The analysis is performed with the integrated value.

According to the invention, the spectral data acquisition is eliminated in each capillary exchange, and the pull-up signal can be decreased without losing the simultaneity between the signal intensity and the signal acquisition.

BRIEF DESCRIPTION OF THE DRAWINGS

FIG. 1 is a perspective view schematically showing a capillary electrophoresis apparatus according to the invention;

FIG. 7 is an explanatory view for explaining a reason why use of the multi-bandpass filter eliminates spectral data acquisition in each capillary exchange in the capillary electrophoresis apparatus according to the invention:

FIG. 9 is an explanatory view for explaining an operation procedure of an analysis method in which the capillary electrophoresis apparatus according to the invention is used;

DESCRIPTION OF THE PREFERRED EMBODIMENTS

Figure 2:
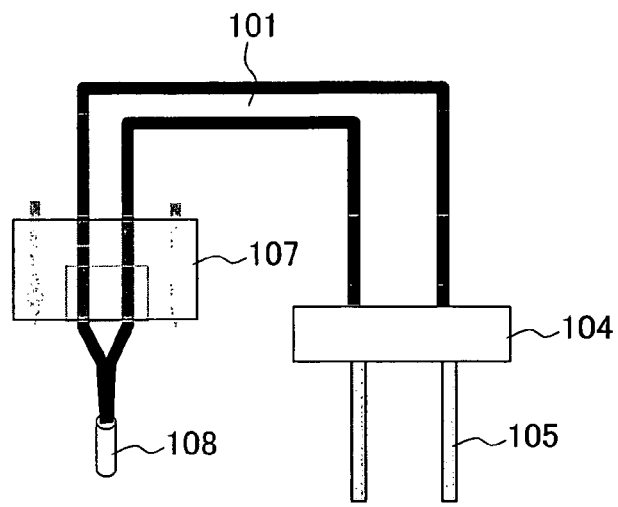
FIG. 2 is a perspective view schematically showing a capillary irradiation unit in the capillary electrophoresis apparatus according to the invention.
Figure 2:
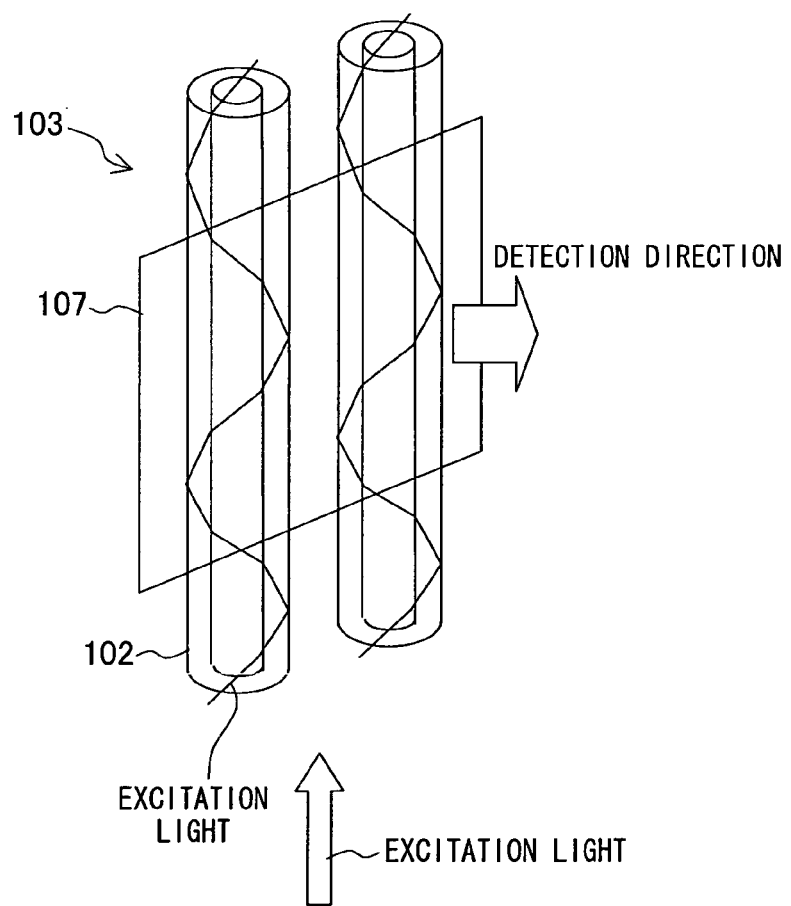

The above and other novel features and advantages of the invention will be described below with reference to the accompanying drawings. However, the drawings are illustrated by way of example only, and the scope of the invention is not limited to the drawings.

Referring to FIG. 1A, a capillary electrophoresis apparatus according to an embodiment of the invention has a capillary array 101, an optical irradiation unit 121, an optical detection unit 131, an automatic sampler unit 141, a pump unit 150, a power supply unit 110, and an oven unit 161. In the capillary electrophoresis apparatus of the embodiment, using plural capillaries filled with electrophoresis mediums, samples are introduced into the capillaries respectively, and sample components in the sample are separated and analyzed by the electrophoresis. For example, plural samples having DNA containing samples are simultaneously analyzed to analyze a base sequence.

The capillary array 101 comprises of plural capillaries 102. In FIG. 1, the capillary array 101 comprises of two capillaries 102. However, for example, the capillary array 101 may include one, four, or eight capillaries 102. The capillary 102 is a thin quartz tube having an inner diameter of tens to hundreds micrometers and an outer diameter of hundreds micrometers, and polyimide coating is performed to a surface of the capillary 102 to enhance strength. Alternatively, fluorine coating may be performed to a portion through which the light propagates.

The capillary array 101 is a detachable replacement part which is replaced by a new one when quality is degraded through predetermined-time analyses to decrease separation capacity. The capillary array 101 is exchanged to the capillary array 101 having a different length when a measuring technique is changed to require a change in length of capillary 102. Therefore, the length of the capillary 102 can arbitrarily be adjusted.

The capillary array 101 has an irradiation unit 103 which is irradiated with the excitation light, a sample introducing end 105 which is used to introduce the sample therethrough, and a capillary head 108 which is formed by bundling the plural capillaries. The sample introducing end 105 is retained by a sample introducing unit 104.

As shown in FIG. 1B, a hollow electrode 106 is inserted into a front edge of the capillary 102, and the front edge of the capillary 102 is slightly projected from the hollow electrode 106. For example, the hollow electrode 106 is formed by a stainless pipe. The capillary head 108 is connected to the pump unit 150.

The optical irradiation unit 121 has a light source 123, a first collective lens 124, an irradiation filter 125, and a second collective lens 126.

In the irradiation unit 103, the capillary 102 is supported on the glass substrate 107. The capillary 102 is irradiated with the excitation light from the optical irradiation unit 121. The light source 123 emits excitation light 122 with which the irradiation unit 103 of the capillary array 101 is irradiated. Usually the laser light source is used as the light source. However, in the embodiment, the light emitting diode (LED) is used as the light source 123.

The first collective lens 124 collects the excitation light 122 emitted from the light source 123. The irradiation filter 125 cuts off an unnecessary wavelength component from the excitation light 122. The second collective lens 126 collects the excitation light 122. The capillary 102 is irradiated with the light collected by the second collective lens 126. In the embodiment, the capillary 102 is irradiated with the excitation light while the excitation light is incident along a capillary axis line or while the excitation light is inclined at a predetermined angle with respect to the capillary axis line.

The sample component separated by the electrophoresis in the capillary 102 is irradiated with the excitation light 122. In a fluorescent material labeled to the sample component, light having a different wavelength is emitted in each sample component. The light is detected with the optical detection unit 131.

The optical detection unit 131 has a first camera lens 132, a multi-bandpass filter 133, a diffraction grating 134, a second camera lens 135, and a two-dimensional detector 136. The optical detection unit 131 will be described in detail later with reference to FIG. 3.

The automatic sampler unit 141 conveys a sample vessel 143, a buffer vessel 144, a cleaning vessel 145, and a waste liquid vessel 146 immediately below the sample introducing unit 104.

The sample vessel 143 is used to hold plural extremely small amount samples, and the sample vessel 143 is conveyed immediately below the sample introducing unit 104 in introducing the sample. For example, the sample is a solution containing a large number of nucleic acids having proper lengths (sizes), fluorescence-labeled by four kinds of nucleotide base molecules.

In the configuration of the sample vessel 143, a scepter which is of a resin sheet is placed on a sample plate including 24-by-16 wells in which the sample of tens microliters can be held in each well, and the scepter is clamped by a holder and a clip. The scepter has through-holes at positions corresponding to the wells, and the through-hole is usually closed to prevent evaporation of the sample in the well. The sample introducing end 105 can come into contact with the sample through the through-hole in introducing the sample. Alternatively, a protective film may adhere to an upper surface of the scepter to prevent evaporation of the sample.

The buffer vessel 144 is used to hold a buffer into which the sample introducing end 105 is dipped, and the buffer vessel 144 is conveyed immediately below the sample introducing unit 104 during the electrophoresis analysis. The buffer vessel 144 is also conveyed immediately below the sample introducing unit 104 in a standby state of the apparatus, and the sample introducing end 105 is dipped in the buffer to prevent the electrophoresis medium in the capillary 102 from drying out.

The cleaning vessel 145 is used to hold a cleaning solution for cleaning the sample introducing end 105, and the cleaning vessel 145 is conveyed immediately below the sample introducing unit 104 during the filling of the electrophoresis medium, during pre run, and after the sample introduction. The sample introducing end 105 is dipped into the cleaning solution in the cleaning vessel, which allows the sample introducing end 105 to be cleaned to avoid contamination.

The waste liquid vessel 146 is used to hold the used electrophoresis medium, and the waste liquid vessel 146 is conveyed immediately below the sample introducing unit 104 during the filling of the electrophoresis medium. During the filling of the electrophoresis medium, the waste liquid vessel 146 receives the used electrophoresis medium discharged from the sample introducing end 105.

The pump unit 150 has a polymer filling block 151, a syringe 152, a tube 153, an electromagnetic valve 154, and a cathode buffer vessel 112. The pump unit 150 automatically fills the capillary 102 with the new electrophoresis medium before the analysis is started.

The polymer filling block 151 has a polymer flow channel 155. The polymer flow channel 155 is communicated with the syringe 152 and the tube 153. The syringe 152 is filled with the electrophoresis medium and the tube 153 comprises the electromagnetic valve 154. The other end of the tube 153 is dipped in the buffer held in the cathode buffer vessel 112. The capillary head 108 is attached to the polymer filling block 151 while pressure-resistant airtight is maintained.

The power supply unit 110 includes a high-voltage power supply 111 which generates a high voltage of about 15 kV. A negative electrode of the high-voltage power supply 111 is connected to the hollow electrode 106, and a positive electrode is grounded through an ammeter 114. One end of the cathode electrode 113 is dipped in the buffer in the cathode buffer vessel 112, and the other end is grounded.

The method of filling the capillary 102 with the electrophoresis medium using the pump unit 150 will briefly be described below. The waste liquid vessel 146 is arranged immediately below the sample introducing unit 104, and the electromagnetic valve 154 is closed to push a plunger of the syringe 152. Therefore, the electrophoresis medium in the syringe 152 flows into the capillary 102 from the capillary head 108 through the polymer flow channel 155. The used electrophoresis medium in the capillary 102 is discharged from the sample introducing end 105 and received by the waste liquid vessel 146.

The method of introducing the sample into the capillary 102 will briefly be described below. The capillary 102, the polymer flow channel 155, and the tube 153 are filled with the electrophoresis medium. The sample vessel 143 is arranged immediately below the sample introducing unit 104, the sample introducing end 105 is dipped in the sample held in the well of the sample vessel 143, and the electromagnetic valve 154 is opened. Therefore, an electric current path is formed between the positive electrode and negative electrode of the high-voltage power supply 111. The electric current path consists of the hollow electrode 106, the sample in the sample vessel 143, an electrophoresis path in the capillary 102, the polymer flow channel 155 of the polymer filling block 151, the tube 153, the buffer in the cathode buffer vessel 112, and the cathode electrode 113. The hollow electrode 106 is set at a negative potential while the cathode electrode 113 is set at a positive potential, and a pulse voltage is applied to the electric current path. Therefore, a negatively charged sample component such as DNA existing in the well is introduced to the electrophoresis path from the sample introducing end 105. The sample introducing method is not limited to the electrophoresis, but the sample may be introduced to the electrophoresis path by pressure or divided injection.

During the electrophoresis analysis, the buffer vessel 144 is arranged immediately below the sample introducing unit 104, and the sample introducing end 105 is dipped in the buffer held in the buffer vessel 144. Therefore, an electric current path is formed between the positive electrode and negative electrode of the high-voltage power supply 111. The electric current path consists of the hollow electrode 106, the buffer in the buffer vessel 144, the electrophoresis path in the capillary 102, the polymer flow channel 155 of the polymer filling block 151, the tube 153, the buffer in the cathode buffer vessel 112, and the cathode electrode 113. The hollow electrode 106 is set at the negative potential while the cathode electrode 113 is set at the positive potential, and the high voltage of about 15 kV is applied to the electric current path. Therefore, an electric field is generated from the irradiation unit 103 to the sample introducing unit 104, and the negatively charged sample component introduced into the electrophoresis path is electrophoresed toward the direction of the irradiation unit 103.

The oven unit 161 controls a temperature of the electrophoresis path which has an influence on an electrophoresis velocity of the sample component. In the embodiment, the oven unit 161 accommodates the capillaries 102 in a temperature controlled oven (not shown). Air whose temperature is kept constant by a temperature control mechanism such as a Peltier device is circulated in the temperature controlled oven to maintain the capillary 102 at a predetermined temperature by a blower mechanism such as a fan.

As described above, in the capillary electrophoresis apparatus of the embodiment, the multi-bandpass filter 133 is provided in optical detection unit 131. When the multi-bandpass filter 133 is provided, the position shift or inclination of the capillary 102 does not have an influence on the fluorescence spectrum acquired by the two-dimensional detector 136. Therefore, in the embodiment, the new spectral data acquisition is eliminated even if the position shift or inclination of the capillary 102 is generated during the capillary exchange.

The irradiation unit 103 will be described in detail with reference to FIG. 2. As shown in FIG. 2A, the glass substrate 107 is provided at a position close to the capillary head 108. As shown in FIG. 2B, the plural capillaries 102 are arrayed on the glass substrate 107. The capillaries 102 are arranged on the glass substrate 107 in parallel with each other to some extent, and the capillaries 102 are arranged in substantially parallel to the glass substrate 107. The term of "to some extent" means that the capillaries 102 may be arranged while inclined at the angle of several degrees, and the term of "substantially" means that the inclination falls in an allowance degree of accuracy. It is necessary that the glass substrate 107 have plane accuracy to some extent.

The excitation light is emitted from the optical irradiation unit 121 along the axis direction of the capillary 102, or the excitation light is emitted along the direction in which the excitation light is inclined at a predetermined angle with respect to the axis direction of the capillary 102. The polyimide coating of the capillary 102 is removed in the irradiation unit 103. Accordingly, the excitation light is totally reflected from outer surfaces of the plural capillaries 102, the excitation light propagates through the capillary 102 to simultaneously excite the samples in the capillaries 102. In the sample in the capillary 102, fluorescent light is generated in a range of several millimeters to tens millimeters by the excitation light propagating through the capillary 102. Thus, the light emission region is linearly formed in the embodiment, so that the light emitting diode (LED) can be used as the excitation light source.

As shown in FIG. 1, the fluorescent light generated from the sample in the capillary 102 is detected with the optical detection unit 131 arranged along the direction perpendicular to the axis direction of the capillary 102.

The optical detection unit 131 will be described with reference to FIG. 3. As shown in FIG. 3A, the optical detection unit 131 includes the first camera lens 132, the multi-bandpass filter 133, the diffraction grating 134, the second camera lens 135, and the two-dimensional detector 136. In the embodiment, the diffraction grating 134 is used as the wavelength dispersion method. The fluorescent light emitted from the light emission region of the capillary 102 is formed in a parallel light flux by the first camera lens 132. The parallel light flux is introduced to the multi-bandpass filter 133. The multi-bandpass filter 133 has discontinuous wavelength transmission characteristics. The wavelength transmission characteristics and a function of the multi-bandpass filter 133 will be described later with reference to FIGS. 4 to 7. The fluorescent light transmitted through the multi-bandpass filter 133 is wavelength-dispersed by the diffraction grating 134, and the fluorescent light is focused on the two-dimensional detector 136 by the second camera lens 135. For example, the two-dimensional detector 136 is formed by a CCD camera. An image signal from the two-dimensional detector 136 is processed to analyze the sample with a computer.

Figure 3:
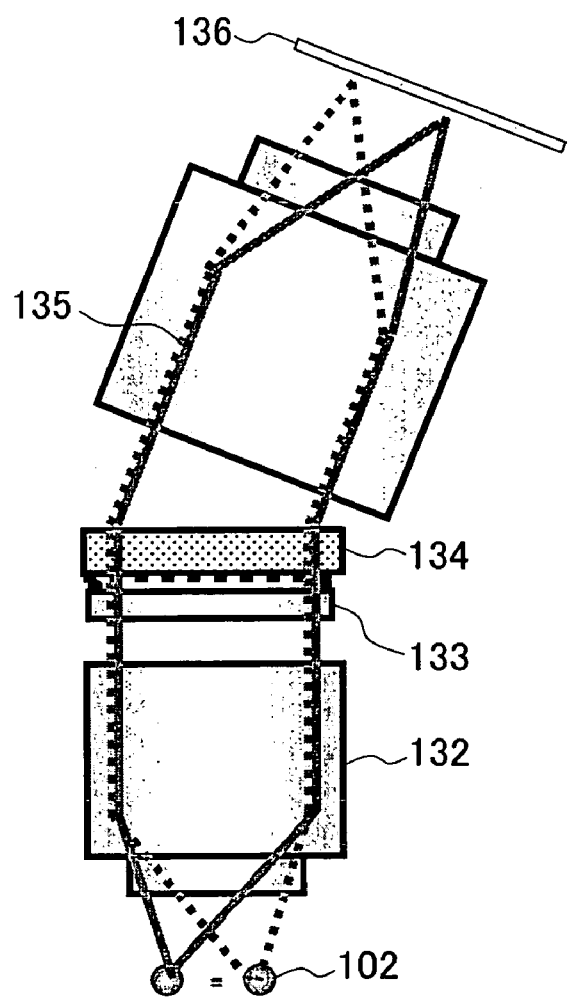
FIG. 3 is a perspective view schematically showing an optical detection unit in the capillary electrophoresis apparatus according to the invention.
Figure 3:
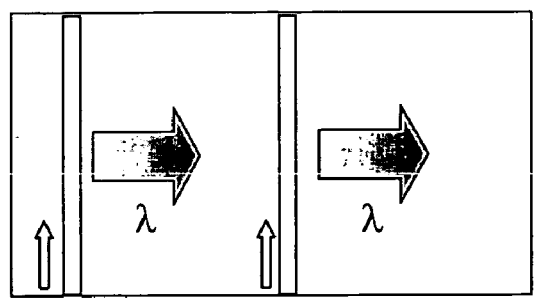

FIG. 3B shows the image acquired by the two-dimensional detector 136. In the embodiment, the two images are acquired corresponding to the two capillaries. A horizontal axis of FIG. 3 indicates a wavelength dispersive direction and a vertical axis indicates a capillary axis direction.

Alternatively, wavelength dispersion means in which prisms are appropriately combined may be used in place of the diffraction grating 134. In place of the CCD camera, the two-dimensional detector 136 may be formed by a one-dimensional detector, a photomultiplier, and a photodiode or the two-dimensional detector 136 may be formed by appropriately combining optical mechanisms.

Figure 4:
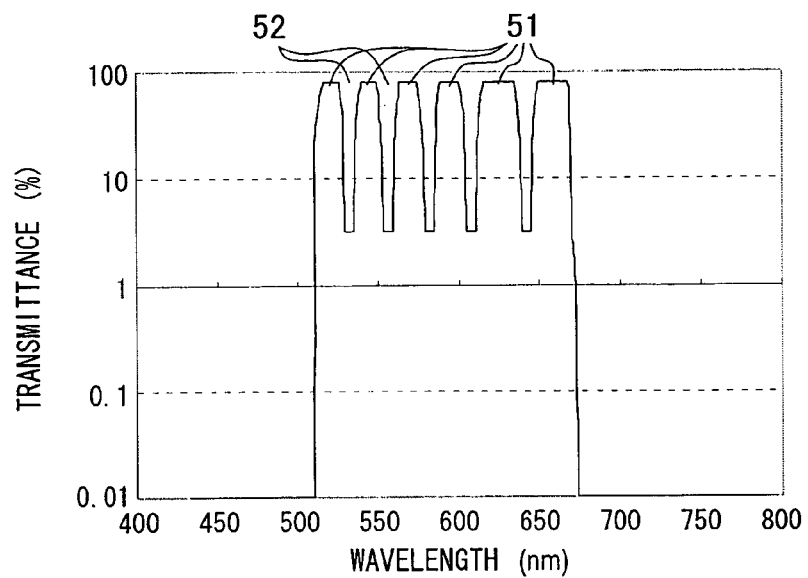
FIG. 4 shows wavelength transmission characteristics of a multi-bandpass filter in the capillary electrophoresis apparatus according to the invention.

FIG. 4 shows the wavelength transmission characteristics of the multi-bandpass filter 133. The multi-bandpass filter 133 of the embodiment cuts off the light having the wavelength longer than a predetermined long-wavelength edge and the light having the wavelength shorter than a predetermined short-wavelength edge. The multi-bandpass filter 133 has six discontinuous transmission regions 51 between the short-wavelength edge and the long-wavelength edge, and the multi-bandpass filter 133 has five discontinuous cutoff regions 52 among the six transmission regions 51. A transmittance is substantially 100% in the transmission regions while the transmittance is not more than 5% in the cutoff region 52. The smaller transmittance is better in the cutoff region 52.

Figure 5A:
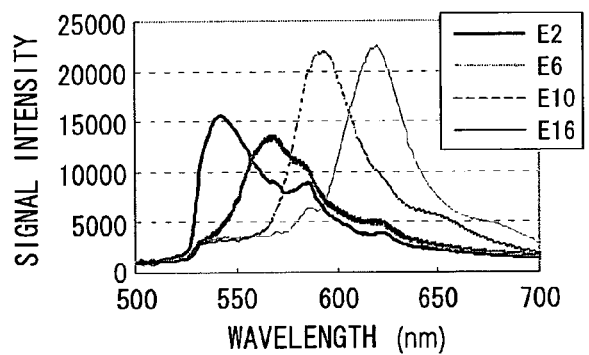
FIG. 5 shows a standard fluorescence spectrum and a fluorescence spectrum transmitted through the multi-bandpass filter in the capillary electrophoresis apparatus according to the invention.

The function of the multi-bandpass filter 133 will be described with reference to FIG. 5. FIG. 5A shows a standard fluorescence spectrum when the capillary is located at a standard position. The standard position shall mean a position of the capillary when the spectral data is acquired. In this case, four-color fluorescent light dyes of E2, E6, E10, and E16 are used. The continuous spectra are obtained by the wavelength dispersion of the fluorescent light beams emitted from the four-color fluorescent light dyes using the diffraction grating 134. The standard fluorescence spectra are used in the actual analysis. The four kinds of DNA can correctly be identified by separating the four-color fluorescence spectra from the detection light of the DNA sample.

Figure 5B:
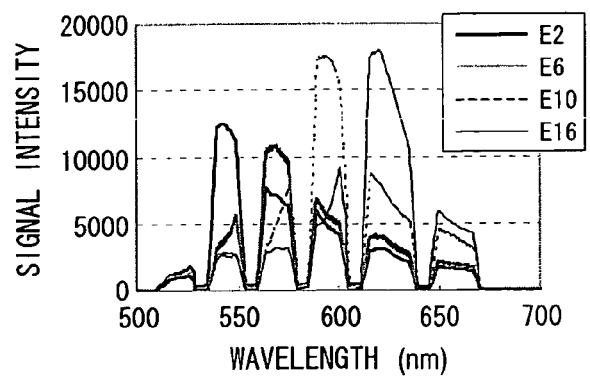

FIG. 5B shows spectra of the four-color fluorescence light dyes transmitted through the multi-bandpass filter 133. As can be seen from comparison with the wavelength transmission characteristics of the multi-bandpass filter 133 of FIG. 4, the fluorescence spectrum is deleted in the regions except for the transmittance region 51.

Figure 6:
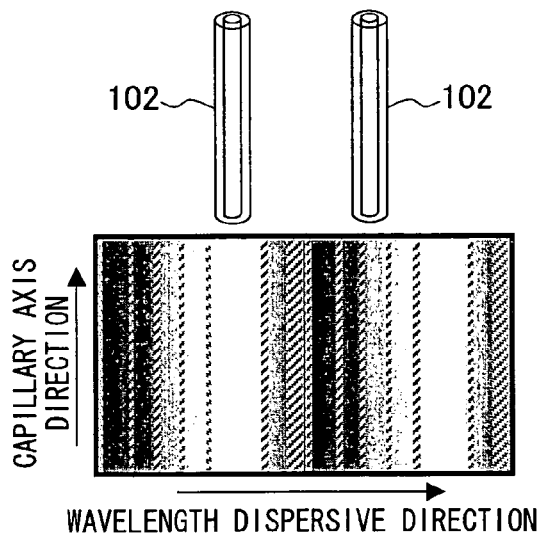
FIG. 6 is an explanatory view for explaining a fluorescence spectrum shift caused by a capillary position shift in the capillary electrophoresis apparatus according to the invention.
Figure 6:
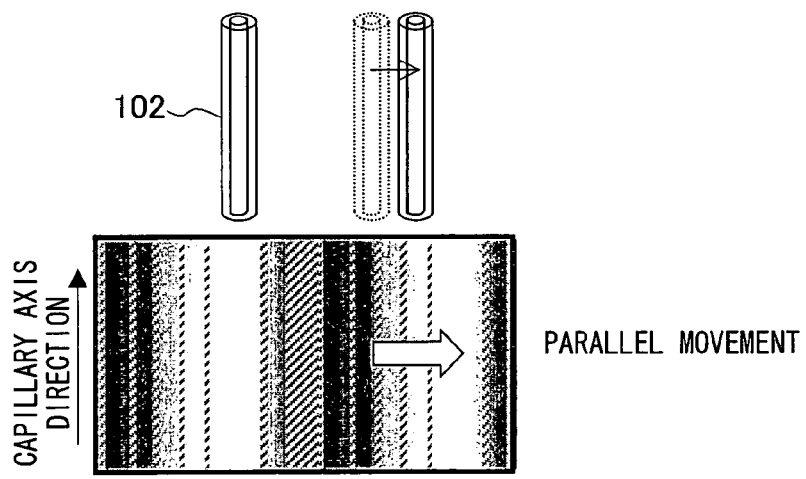
Figure 6:
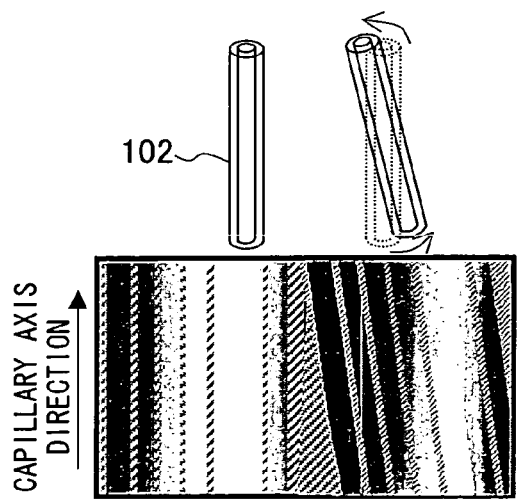

A change in capillary image on the image of the two-dimensional detector 136 when the position shift is generated by the capillary exchange will be described with reference to FIG. 6. The fluorescence spectrum image position focused on the two-dimensional detector 136 is determined by a relative position between the capillary 102 and the two-dimensional detector 136. It is assumed that the two-dimensional detector 136 is fixed. When the position of the capillary 102 is changed by the capillary exchange, the position of the fluorescence spectrum image is moved in parallel to a wavelength dispersive direction or to a capillary axis direction although the shape of the fluorescence spectrum image is not changed on the image of the two-dimensional detector 136. The same holds true for the case where the multi-bandpass filter 133 is used like the embodiment.

FIG. 6A shows the two capillaries 102 and capillary images at the standard position. The standard position is the capillary position in the spectral data acquisition, and the capillary 102 has neither position shift nor inclination at the standard position.

FIG. 6B shows the case where the position of one of the capillaries 102 is shifted toward the wavelength dispersive direction with respect to the standard position due to the capillary exchange. When the position of the capillary 102 is changed due to the capillary exchange, the position of the fluorescence spectrum image is moved in parallel to the wavelength dispersive direction on the image of the two-dimensional detector 136 although the shape of the fluorescence spectrum image is not changed on the image.

FIG. 6C shows the case where the position of one of the capillaries 102 is inclined from the standard position with respect to the capillary axis due to the capillary exchange. In the case where the capillary 102 is inclined with respect to the capillary axis, it can be assumed that the capillary 102 consists of plural short portions which are sequentially shifted in the wavelength dispersive direction.

The reason why the use of the multi-bandpass filter 133 eliminates the spectral data acquisition in each capillary exchange will be described below with reference to FIG. 7. FIGS. 7A, 7B, and 7C show the conventional technique in which the multi-bandpass filter 133 is not used but the usual detection filter is used. FIG. 7A shows a wavelength region detected by the two-dimensional detector 136. The detection filter transmits the fluorescent light beams having all the wavelength regions used for the analysis. Accordingly, the two-dimensional detector 136 detects all the wavelength regions.

FIG. 7B shows a standard fluorescence spectrum detected by the two-dimensional detector 136. Usually an integrated value of the signal in a predetermined wavelength region including a fluorescence spectrum peak is used in the wavelength calibration. For example, an imaging region of the two-dimensional detector 136 is divided into six regions in the wavelength direction. The fluorescence spectrum signal is integrated in the region where the fluorescence spectrum peak exists. For example, the fluorescence spectrum signal is integrated in all the regions, and it is judged that the fluorescence spectrum peak exists in the region where the integrated value becomes the maximum. In the embodiment of FIG. 7, the fluorescence spectrum peak exists in the second region form the left. Accordingly, the integrated value of the fluorescence spectrum signal in the second region from the left is used in the wavelength calibration. One imaging region corresponds to several pixels of the two-dimensional detector 136.

FIG. 7C shows a fluorescence spectrum of the analysis sample detected by the two-dimensional detector 136 after the capillary exchange. The capillary position is shifted from the standard position due to the capillary exchange. Accordingly, when the standard fluorescence spectrum of FIG. 7B is compared to the fluorescence spectrum of FIG. 7C, the fluorescence spectrum of FIG. 7C is shifted in the wavelength dispersive direction. In FIG. 7C, the six regions set in the imaging regions of the two-dimensional detector 136 are similar to those of FIG. 7B. In the embodiment of FIG. 7C, the fluorescence spectrum peak exists in the second region from the left. However, because the position is shifted in the fluorescence spectrum of FIG. 7C, the fluorescence spectrum signal in the second region from the left of FIG. 7C differs from the fluorescence spectrum signal in the second region from the left of FIG. 7B in the integrated value. Accordingly, the pull-up signal is generated to cause an error when the integrated value of the fluorescence spectrum signal in the second region from the left of FIG. 7C is used in the wavelength calibration. In this case, the spectral data acquisition is required in the capillary exchange.

FIGS. 7D, 7E, and 7F show the embodiment in which the multi-bandpass filter 133 is used. FIG. 7D shows a wavelength region detected by the two-dimensional detector 136. Because the multi-bandpass filter 133 transmits only the fluorescent light beams having the transmission regions, the two-dimensional detector 136 detects the discontinuous wavelength regions. That is, the detection signals do not exist substantially in the wavelength regions corresponding to the cutoff regions of the multi-bandpass filter 133.

FIG. 7E shows a standard fluorescence spectrum detected by the two-dimensional detector 136. The imaging region of the two-dimensional detector 136 is divided into six regions in the wavelength direction. The six regions correspond to the wavelength transmission region periods of the multi-bandpass filter 133 shown in FIG. 4. In the embodiment of FIG. 7D, the fluorescence spectrum peak exists in the second region from the left. Accordingly, the integrated value of the fluorescence spectrum signal in the second region from the left is used in the wavelength calibration.

FIG. 7F shows a fluorescence spectrum of the analysis sample detected by the two-dimensional detector 136 after the capillary exchange. In FIG. 7F, the six regions set in the imaging regions of the two-dimensional detector 136 are similar to those of FIG. 7E. In the embodiment of FIG. 7F, the fluorescence spectrum peak exists in the second region from the left.

The capillary position is shifted from the standard position due to the capillary exchange. Accordingly, when the standard fluorescence spectrum of FIG. 7E is compared to the fluorescence spectrum of FIG. 7F, the fluorescence spectrum of FIG. 7F is shifted in the wavelength dispersive direction. However, both ends of the fluorescence spectrum signal in each region are deleted corresponding to each cutoff region of the multi-bandpass filter 133.

Because the fluorescence spectrum signal in the second region from the left of FIG. 7F is substantially similar to the fluorescence spectrum signal in the second region from the left of FIG. 7E in the integrated value, the pull-up signal is not generated even if the fluorescence spectrum signal in the second region from the left of FIG. 7F is used in the wavelength calibration. Accordingly, the error is not caused. Thus, in the embodiment, the spectral data acquisition is eliminated in the capillary exchange.

With increasing wavelength range of the cutoff region in the multi-bandpass filter 133, a larger tolerance can be ensured in the position shift of the capillary 102.

Figure 8A:
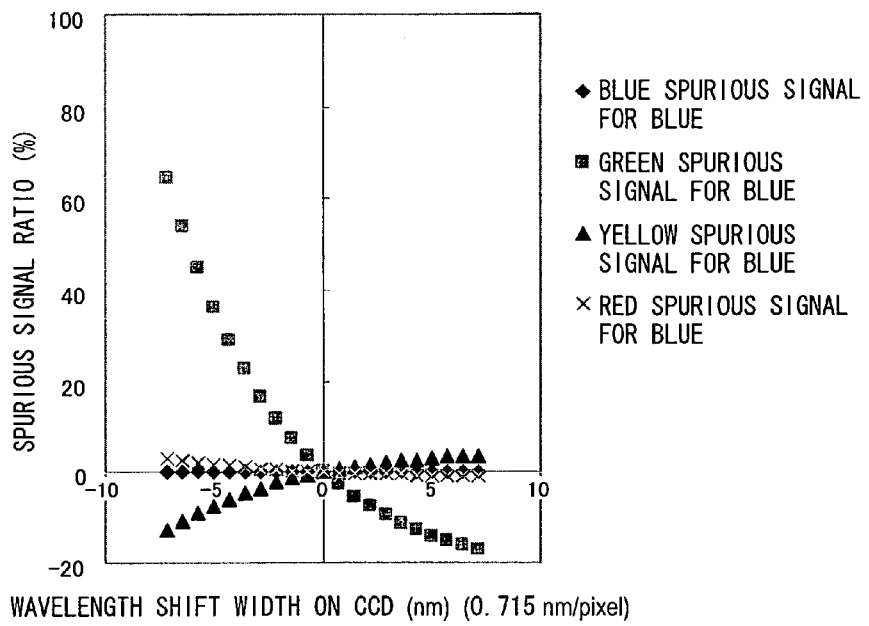
FIG. 8 shows a relationship between an amount of fluorescence spectrum shift and a pull-up signal, which are generated due to the capillary position shift in the capillary electrophoresis apparatus according to the invention.

FIG. 8 shows a relationship between the amount of fluorescence spectrum shift and the pull-up signal, which are generated due to the capillary position shift. dR110 is used as the fluorescence dye. A horizontal axis indicates an amount of capillary position shift (nm), and a vertical axis indicates a pull-up signal rate (%). FIG. 8A shows the conventional technique in which the multi-bandpass filter 133 is not used but the usual detection filter is used. In order that the pull-up signal is suppressed to 1% or less, it is necessary that the shift amount be not more than the wavelength of 0.2 nm in the imaging region of the two-dimensional detector. This means that the error is not more than 1 µm in the capillary attachment position. Because the structure satisfying this specification is hardly realized, the spectral data acquisition is required in each capillary attachment.

Figure 8B:
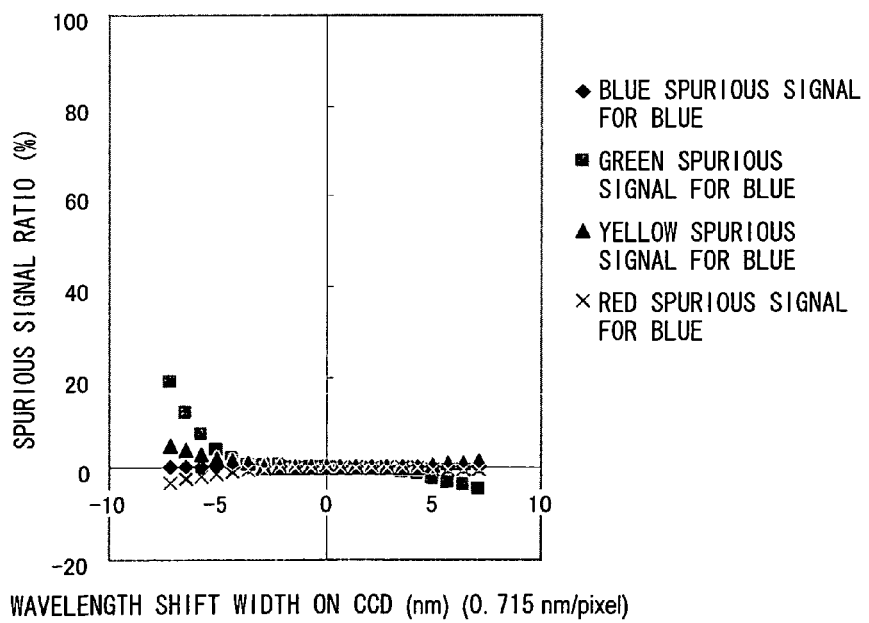

FIG. 8B shows the embodiment in which the multi-bandpass filter 133 is used. In order that the pull-up signal is suppressed to 1% or less, it is necessary that the shift amount be not more than the wavelength of 5.0 nm in the imaging region of the two-dimensional detector. This means that the error not more than tens micrometers can be allowed for in the capillary attachment position. Because the structure satisfying this specification can be realized, the spectral data acquisition is eliminated in each capillary attachment.

The detailed operation procedure of the analysis method with the capillary electrophoresis apparatus according to the invention will be described with reference to FIG. 9. The spectral data is acquired in Step 200. Usually the spectral data acquisition is performed before shipment in a manufacturing plant. For example, the standard fluorescence spectra are acquired by electrophoresing the wavelength-calibrated DNA samples labeled by four-color fluorescent light dyes. When the standard fluorescence spectrum is acquired as the spectral data, the electrophoresis analysis is performed as follow.

The basic procedure of the electrophoresis analysis includes pre-analysis preparation of Step 201, analysis start of Step 202, filling of electrophoresis medium of Step 203, pre run of Step 204, sample introduction of Step 205, electrophoresis of Step 206, and analysis of Step 207. The basic procedure of the electrophoresis analysis is performed on the user side.

An operator performs the pre-analysis preparation of Step 201. The capillary arrays 101 are exchanged, when the capillary 102 is degraded or when the change in length of the capillary 102 is required. In this case, the capillaries are exchanged. The buffer vessel 144 and the cathode buffer vessel 112 are filled with the buffer. A commercially available electrolyte fluid for electrophoresis can be cited as an example of the buffer. Then, the sample which is of the analysis target is dispensed into the wells of the sample vessel 143. For example, the sample is a Polymerase Chain Reaction (PCR) metabolite of DNA. The cleaning solution is dispensed in the cleaning vessel 145. For example, the cleaning solution is pure water. The electrophoresis medium is injected into the syringe 152. A commercially available polyacrylamide resolving gel for electrophoresis can be cited as an example of the electrophoresis medium.

The operator starts the analysis of Step 202. In the filling of electrophoresis medium of Step 203, the capillary 102 is filled with the new electrophoresis medium to form the electrophoresis path. The automatic sampler unit conveys the waste liquid vessel 146 immediately below the sample introducing unit 104. Then, the syringe 152 is driven to fill the capillary 102 with the new electrophoresis medium, and the used electrophoresis medium is disposed of into the waste liquid vessel 146. Finally, the automatic sampler unit conveys the cleaning vessel 145 immediately below the sample introducing unit 104, the sample introducing end 105 is dipped in the cleaning solution to clean the sample introducing end 105 which becomes dirty with the electrophoresis medium.

In the pre run of Step 204, a predetermined voltage is applied to the electrophoresis medium, and the electrophoresis medium is put in the state suitable to the electrophoresis. The automatic sampler unit conveys the buffer vessel 144 immediately below the sample introducing unit 104, and the sample introducing end 105 is dipped in the buffer to form the electric current path. Then, the power supply unit applies the voltage ranging from several kilovolts to tens kilovolts to the electrophoresis medium for several minutes to tens minutes. Therefore, the electrophoresis medium is put into the state suitable to the electrophoresis. Finally, the automatic sampler unit conveys the cleaning vessel 145 immediately below the sample introducing unit 104, the sample introducing end 105 is dipped in the cleaning solution to clean the sample introducing end 105 which becomes dirty with the buffer.

In the sample introduction of Step 205, the sample component is introduced into the electrophoresis path. The automatic sampler unit conveys the sample vessel 143 immediately below the sample introducing unit 104, and the sample introducing end 105 is dipped in the sample held in the wells of the sample vessel 143. Therefore, the electric current path is formed, and the sample component can be introduced into the electrophoresis path. The power supply unit applies the pulse voltage to the electric current path, and the sample component is introduced into the electrophoresis path. Finally, the automatic sampler unit conveys the cleaning vessel 145 immediately below the sample introducing unit 104, the sample introducing end 105 is dipped in the cleaning solution to clean the sample introducing end 105 which becomes dirty with the sample.

In the electrophoresis of Step 206, each sample component contained in the sample is separated and analyzed by the electrophoresis. The automatic sampler unit conveys the buffer vessel 144 immediately below the sample introducing unit 104, and the sample introducing end 105 is dipped in the buffer to form the electric current path. Then, the power supply unit applies the high voltage of about 15 kV to the electric current path to generate the electric field in the electrophoresis path.

The sample components in the electrophoresis path are migrated to the irradiation unit 103 at velocities according to the characteristics of each sample component by the generated electric field. That is, the sample components are separated by the difference in migration velocity. The sample component reaching the irradiation unit 103 is sequentially detected. For example, in the case where the sample contains a large number of DNAs having different base lengths, the difference in migration velocity is generated by the base length, and DNA having the shorter base length first reaches the irradiation unit 103. The irradiation unit 103 irradiates the sample components with the excitation light. In each DNA, an end of base sequence labeled by the fluorescent light emits the fluorescent light in the order in which the end of base sequence reaches the irradiation unit 103.

The two-dimensional detector 136 detects the fluorescence spectrum. The detection of the fluorescence spectrum is already described with reference to FIG. 7.

In the analysis of Step 207, the data acquired by the electrophoresis is normalized to acquire the target wavelength dispersion data by utilizing the spectral data acquired in Step 200. When the spectral data is incorrect, the pull-up signal is generated to decrease the reliability of the analysis result.

When the predetermined amount of data is taken, the process is ended. The voltage application is stopped to terminate the electrophoresis analysis. Thus, the sequence of analysis procedure is described above. In the case where the analysis is further performed, the analysis procedure is repeated from the filling of electrophoresis medium of Step 203. In the case where another analysis is performed, the analysis procedure is repeated from the pre-analysis preparation of Step 201. In both the cases, the spectral data acquisition of Step 200 is not repeated.

Figure 10:
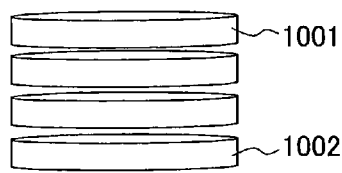
FIG. 10 shows a configuration example of the multi-bandpass filter in the capillary electrophoresis apparatus according to the invention.
Figure 10:
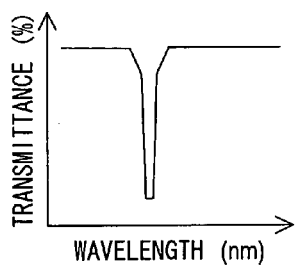
Figure 10:
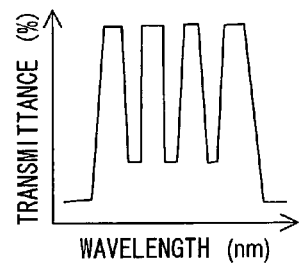
Figure 10:
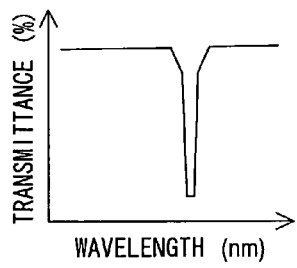
Figure 10:
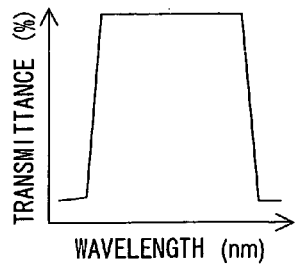

FIG. 10 shows another embodiment of the multi-bandpass filter. As shown in FIG. 10A, the multi-bandpass filter of the embodiment includes three notch filters 1001 and one bandpass filter 1002. FIG. 10B shows wavelength transmission characteristics of the first notch filter 1001, and FIG. 10C shows wavelength transmission characteristics of the second notch filter 1001. As shown in FIGS. 10B and 10C, the light transmittance is not more than 5% in predetermined narrow wavelength regions, and the light is completely cut off in the regions except for the narrow wavelength regions. However, the narrow wavelength regions differ from each other in the notch filters, and the narrow wavelength regions are sequentially shifted. In the third notch filter 1001, the narrow wavelength region is further shifted.

FIG. 10D shows wavelength transmission characteristics of the bandpass filter 1002. A bandpass filter transmits a light beam having a predetermined wavelength region, while completely cutting off other light beams except for the light beam having the predetermined wavelength region.

FIG. 10E shows the wavelength characteristics of the multi-bandpass filter of the embodiment. The wavelength characteristics are formed by laminating the wavelength transmission characteristics of the three notch filters 1001 and the wavelength transmission characteristics of the one bandpass filter 1002. The wavelength transmission characteristics similar to those of the multi-bandpass filter shown in FIG. 4 are acquired in the wavelength transmission characteristics of the multi-bandpass filter of the embodiment. Alternatively, at least four notch filters may be used.

Figure 11:
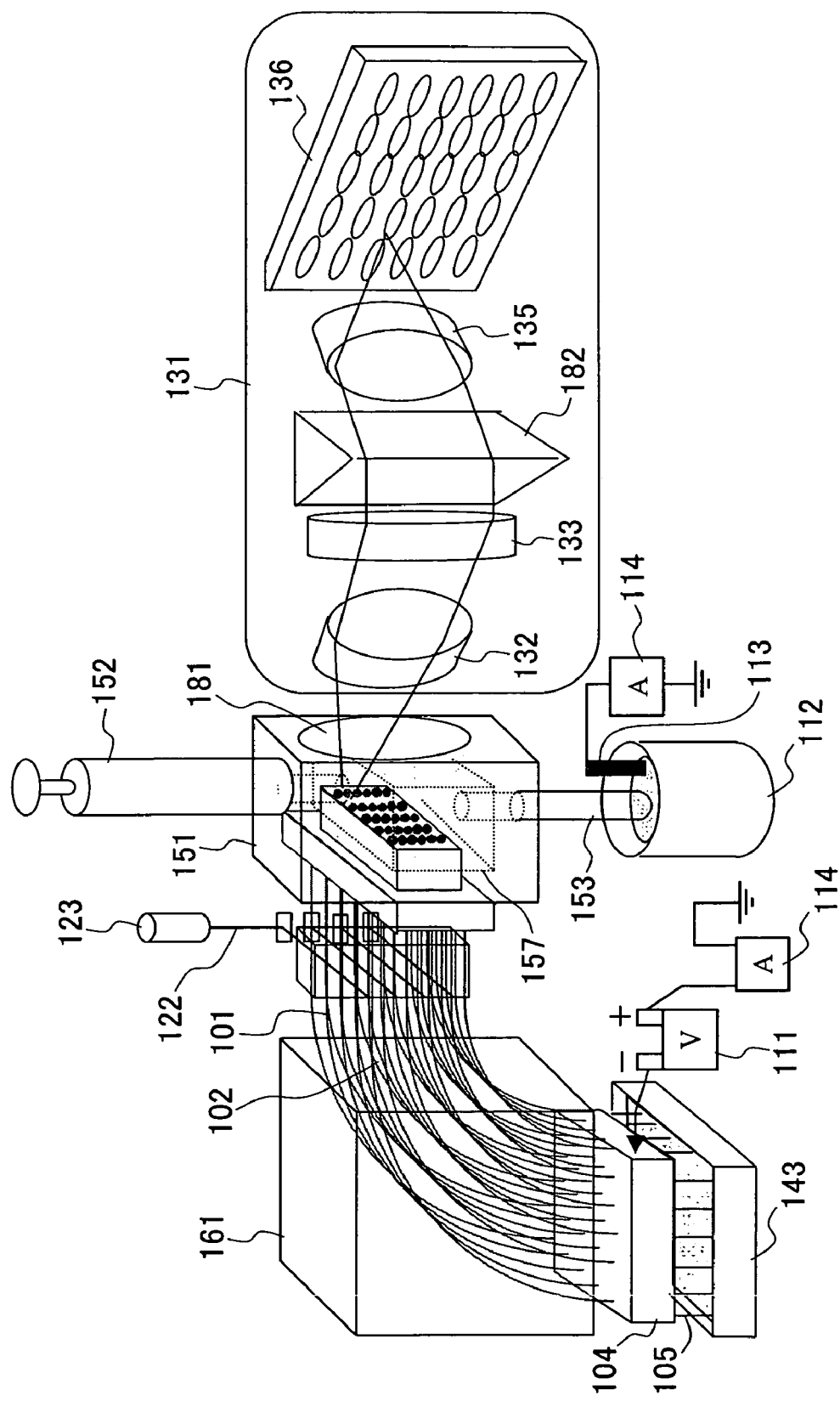
FIG. 11 is a perspective view schematically showing a capillary electrophoresis apparatus according to another embodiment of the invention.

Referring to FIG. 11, the capillary electrophoresis apparatus of another embodiment will be described. The fluorescent light from the light emission region of the capillary 102 is emitted from a tail end of the capillary 102 in the capillary electrophoresis apparatus of the embodiment. The optical detection unit 131 is arranged along the capillary axis line such that the fluorescent light can be detected from the tail end of the capillary.

The capillary 102 is irradiated with the excitation light 122 emitted from the light source 123, and the detection light is emitted from the tail end of the capillary. The detection light reaches the optical detection unit 131 through a detection window 181 of the pump unit 150.

The optical detection unit 131 of the embodiment includes the first camera lens 132, the multi-bandpass filter 133, a prism 182, the second camera lens 135, and the two-dimensional detector 136. In the embodiment, the prism 182 is used as the wavelength dispersion device in place of the diffraction grating. The fluorescent light emitted from the tail end of the capillary 102 is formed in the parallel light flux by the first camera lens 132. The parallel light flux is guided to the multi-bandpass filter 133. The multi-bandpass filter 133 has the plural discontinuous wavelength transmission characteristics. The fluorescent light transmitted through the multi-bandpass filter 133 is wavelength-dispersed by the prism 182 and focused on the two-dimensional detector 136 by the second camera lens 135. For example, the two-dimensional detector 136 is formed by the CCD camera. The image signal transmitted from the two-dimensional detector 136 is processed to analyze the sample with a computer.

In the capillary electrophoresis apparatus of the embodiment, sometimes the capillary position is also shifted due to the capillary exchange. However, because multi-bandpass filter 133 is used as described above, the fluorescence spectrum signal detected by the two-dimensional detector is not affected by the position shift or inclination of the capillary. Therefore, the pull-up signal generation caused by the position shift or inclination of the capillary can be prevented.

The invention is not limited to the capillary electrophoresis apparatus. For example, the invention can be applied to both a slab type electrophoresis apparatus in which the electrophoresis path is formed by two plates and a micro-chip type electrophoresis apparatus in which the flow channel is formed in a resin or a glass plate. The invention can further be applied to a spectral photometer in which the sample fluorescent light is dispersed by the diffraction grating, the prism, or the like.

The embodiments of the invention are described above. However, the invention is not limited to the above embodiments, but it is understood for those skilled in the art that various changes and modifications can be made without departing from the scope of the invention. The appropriate combination of the embodiments should also be included in the invention.

What is claimed is:
1. A capillary electrophoresis apparatus having:
a capillary;
an optical irradiation system which irradiates the capillary with excitation light; and
an optical detection system comprising:
a wavelength dispersion device configured to disperse fluorescent light from the capillary along a direction perpendicular to the capillary axis, a two-dimensional detector configured to detect a fluorescence spectrum image acquired from the wavelength dispersion device, and a multi-bandpass filter having a plurality of predetermined discontinuous wavelength transmission regions, wherein:

the multi-bandpass filter cuts off the fluorescent light having a wavelength longer than a predetermined long-wavelength edge and the fluorescent light having a wavelength shorter than a predetermined short-wavelength edge, the multi-bandpass filter has at least one discontinuous cutoff region between the predetermined long-wavelength edge and the predetermined short-wavelength edge, the two-dimensional detector is a two-dimensional charged coupled-device device (CCD) camera configured to form images from the capillary in the wavelength dispersion direction and the capillary axis direction, the capillary axis direction being orthogonal relative to the wavelength dispersion direction, the optical detection system calculates an integrated value of a signal of the fluorescence spectrum for each of the wavelength transmission regions of the multi-bandpass filter, and excitation light irradiating the capillary propagates in the capillary axis direction.

2. A capillary electrophoresis apparatus according to claim 1, wherein a signal detection area of the two-dimensional detector is divided into a plurality of regions corresponding to the wavelength transmission regions of the multi-bandpass filter.

3. A capillary electrophoresis apparatus according to claim 2, wherein an integrated value of a signal of the fluorescence spectrum is determined in a region including a fluorescence spectrum peak of a sample in the plurality of regions.

4. A capillary electrophoresis apparatus according to claim 2, wherein the integrated value of the signal of the fluorescence spectrum is determined in each of the plurality of regions, and it is judged that the region where the integrated value becomes the maximum is the region where the fluorescence spectrum peak exists.

5. A capillary electrophoresis apparatus according to claim 1, wherein the multi-bandpass filter includes a plurality of notch filters and one bandpass filter.

6. A capillary electrophoresis apparatus according to claim 1, wherein the optical irradiation system irradiates the capillary with the excitation light from a direction along an axis line of the capillary or a direction in which the excitation light is inclined at a predetermined angle with respect to the axis line of the capillary.

7. A capillary electrophoresis apparatus according to claim 1, wherein the optical irradiation system has a light emitting diode which is of an excitation light source.

8. An analysis apparatus having:

a capillary;

an optical irradiation unit which irradiates the capillary with excitation light;

an optical detection system which has a wavelength dispersion device, a multi-bandpass filter, and a two-dimensional detector, the wavelength dispersion device dispersing fluorescent light from the capillary along a direction perpendicular to the capillary axis, the multi-bandpass filter transmitting only a plurality of predetermined discontinuous wavelength transmission regions in fluorescence spectra acquired from the wavelength dispersion device, the two-dimensional detector detecting a fluorescence spectrum image transmitted through the multi-bandpass filter, wherein:

a sample is analyzed from a fluorescence spectrum of the sample detected by the optical detection unit, the multi-bandpass filter cuts off the fluorescent light having a wavelength longer than a predetermined long-wavelength edge and the fluorescent light having a wavelength shorter than a predetermined short-wavelength edge, and the multi-bandpass filter has at least one discontinuous cutoff region between the predetermined long-wavelength edge the predetermined short-wavelength edge, the two-dimensional detector is a two-dimensional charged coupled-device device (CCD) camera configured to form images from the capillary in the wavelength dispersion direction and the capillary axis direction, the capillary axis direction being orthogonal relative to the wavelength dispersion direction, optical detection system calculates an integrated value of a signal of the fluorescence spectrum for each of the wavelength transmission regions of the multi-bandpass filter, and excitation light irradiating the capillary propagates in the capillary axis direction.

9. An analysis apparatus according to claim 8, wherein a signal detection area of the two-dimensional detector is divided into a plurality of regions corresponding to wavelength transmission regions of the multi-bandpass filter.

10. An analysis apparatus according to claim 8, wherein an integrated value of a signal of the fluorescence spectrum is determined in a region including a fluorescence spectrum peak of a sample in the plurality of regions.

11. A capillary electrophoresis method in which a sample is electrophoresed in a capillary, the capillary is irradiated with excitation light, fluorescent light from the capillary is dispersed along a direction perpendicular to the capillary axis to generate a fluorescence spectrum, an image of the fluorescence spectrum is detected by a two-dimensional detector, and the sample is analyzed based on the detection result, wherein:

the two-dimensional detector detects the image of the fluorescence spectrum after the fluorescence spectrum is transmitted through a multi-bandpass filter having a plurality of predetermined discontinuous wavelength transmission regions, the two-dimensional detector is a two-dimensional charged coupled-device device (CCD) camera configured to form images from the capillary in the wavelength dispersion direction and the capillary axis direction, the capillary axis direction being orthogonal relative to the wavelength dispersion direction, the multi-bandpass filter cuts off the fluorescent light having a wavelength longer than a predetermined long-wavelength edge and the fluorescent light having a wavelength shorter than a predetermined short-wavelength edge, the multi-bandpass filter has at least one discontinuous cutoff region between the predetermined long-wavelength edge and the predetermined short-wavelength edge, and wherein an optical detection system calculates an integrated value of a signal of the fluorescence spectrum for each of the wavelength transmission regions of the multi-bandpass filter, and excitation light irradiating the capillary propagates in the capillary axis direction.

12. A capillary electrophoresis method according to claim 11,
wherein a signal detection area of the two-dimensional detector is divided into a plurality of regions corresponding to wavelength transmission regions of the multi-bandpass filter.

13. A capillary electrophoresis method according to claim 11,
wherein an integrated value of a signal of the fluorescence spectrum is determined in a region including a fluorescence spectrum peak of an analysis sample in the plurality of regions.

14. A capillary electrophoresis method according to claim 11, wherein the integrated value of the signal of the fluorescence spectrum is determined in each of the plurality of regions, and it is judged that the region where the integrated value becomes the maximum is the region where the fluorescence spectrum peak exists.

15. A capillary electrophoresis apparatus having:
a capillary;
an optical irradiation system which irradiates the capillary with excitation light; and
an optical detection system which includes a wavelength dispersion device and a two-dimensional detector, the wavelength dispersion device dispersing fluorescent light from the capillary along a direction perpendicular to the capillary axis, the two-dimensional detector detecting a fluorescence spectrum image acquired from the wavelength dispersion device,
wherein:
the optical detection system has a multi-bandpass filter having a plurality of predetermined discontinuous wavelength transmission regions,
the multi-bandpass filter has at least one notch filter and at least one bandpass filter,
the bandpass filter cutting off the fluorescent light having a wavelength longer than a predetermined long-wavelength edge and the fluorescent light having a wavelength shorter than a predetermined short-wavelength edge,
the at least one notch filter and the at least one bandpass filter are positioned sequentially along an axis,
the two-dimensional detector is a two-dimensional charged coupled-device device (CCD) camera configured to form images from the capillary in the wavelength dispersion direction and the capillary axis direction, the capillary axis direction being orthogonal relative to the wavelength dispersion direction,
the optical detection system calculates an integrated value of a signal of the fluorescence spectrum for each of the wavelength transmission regions of the multi-bandpass filter, and
excitation light irradiating the capillary propagates in the capillary axis direction.

16. A capillary electrophoresis apparatus according to claim 15, wherein a signal detection area of the two-dimensional detector is divided into a plurality of regions corresponding to the wavelength transmission regions of the multi-bandpass filter.

17. A capillary electrophoresis apparatus according to claim 16, wherein an integrated value of a signal of the fluorescence spectrum is determined in a region including a fluorescence spectrum peak of a sample in the plurality of regions.

18. A capillary electrophoresis apparatus according to claim 16, wherein the integrated value of the signal of the fluorescence spectrum is determined in each of the plurality of regions, and it is judged that the region where the integrated value becomes the maximum is the region where the fluorescence spectrum peak exists.

19. A capillary electrophoresis apparatus according to claim 15, wherein the optical irradiation system irradiates the capillary with the excitation tight from a direction along an axis line of the capillary or a direction in which the excitation light is inclined at a predetermined angle with respect to the axis line of the capillary.

20. A capillary electrophoresis apparatus according to claim 15, wherein the optical irradiation system has a light emitting diode which is of an excitation light source.

21. An analysis apparatus having: a capillary;
an optical irradiation system which irradiates the capillary with excitation light;
an optical detection unit which has a wavelength dispersion device, a multi-bandpass filter, and a two-dimensional detector, the wavelength dispersion device dispersing fluorescent light from the capillary along a direction perpendicular to the capillary axis, the multi-bandpass filter transmitting only a plurality of predetermined discontinuous wavelength transmission regions in fluorescence spectra acquired from the wavelength dispersion device, the two-dimensional detector detecting a fluorescence spectrum image transmitted through the multi-bandpass filter,
wherein:
a sample is analyzed from a fluorescence spectrum of the sample detected by the optical detection unit,
the multi-bandpass filter has at least one notch filter and at least one bandpass filter,
the bandpass filter cutting off the fluorescent light having a wavelength longer than a predetermined long-wavelength edge and the fluorescent light having a wavelength shorter than a predetermined short-wavelength edge,
the at least one notch filter and the at least one bandpass filter are positioned sequentially along an axis,
the two-dimensional detector is a two-dimensional charged coupled-device device (CCD) camera configured to form images from the capillary in the wavelength dispersion direction and the capillary axis direction, the capillary axis direction being orthogonal relative to the wavelength dispersion direction,
the optical the detection system calculates an integrated value of a signal of the fluorescence spectrum for each of the wavelength transmission regions of the multi-bandpass filter, and
excitation light irradiating the capillary propagates in the capillary axis direction.

22. An analysis apparatus according to claim 21, wherein a signal detection area of the two-dimensional detector is divided into a plurality of regions corresponding to wavelength transmission regions of the multi-bandpass filter.

23. An analysis apparatus according to claim 21, wherein an integrated value of a signal of the fluorescence spectrum is determined in a region including a fluorescence spectrum peak of a sample in the plurality of regions.

24. A capillary electrophoresis method in which a sample is electrophoresed in a capillary, the capillary is irradiated with excitation light, fluorescent light from the capillary is dispersed to generate a fluorescence spectrum, an image of the fluorescence spectrum is detected by a two-dimensional detector, and the sample is analyzed based on the detection result,
wherein:

the two-dimensional detector detects the image of the fluorescence spectrum after the fluorescence spectrum is transmitted through a multi-bandpass filter having a plurality of discontinuous wavelength transmission regions, the multi-bandpass filter has at least one notch filter and at least one bandpass filter, the bandpass filter cutting off the fluorescent light having a fluorescent wavelength longer than a predetermined long-wavelength edge and the fluorescent light having a wavelength shorter than a predetermined short-wavelength edge, the at least one notch filter and the at least one bandpass filter are positioned sequentially along an axis, the two-dimensional detector is a two-dimensional charged coupled-device device (CCD) camera configured to form images from the capillary in the wavelength dispersion direction and the capillary axis direction, the capillary axis direction being orthogonal relative to the wavelength dispersion direction, an optical detection system calculates an integrated value of a signal of the fluorescence spectrum for each of the wavelength transmission regions of the multi-bandpass filter, and excitation light irradiating the capillary propagates in the capillary axis direction.

25. A capillary electrophoresis method according to claim 24, wherein a signal detection area of the two-dimensional detector is divided into a plurality of regions corresponding to wavelength transmission regions of the multi-bandpass filter.

26. A capillary electrophoresis method according to claim 24, wherein an integrated value of a signal of the fluorescence spectrum is determined in a region including a fluorescence spectrum peak of an analysis sample in the plurality of regions.

27. A capillary electrophoresis method according to claim 24, wherein the integrated value of the signal of the fluorescence spectrum is determined in each of the plurality of regions, and it is judged that the region where the integrated value becomes the maximum is the region where the fluorescence spectrum peak exists.

* * * * *